(12) United States Patent
Vinogradov et al.

(10) Patent No.: US 10,073,066 B2
(45) Date of Patent: Sep. 11, 2018

(54) NON-CONTACT MAGNETOSTRICTIVE SENSOR FOR GUIDED WAVE MONITORING OF WIRE ROPES OR OTHER SOLID FERROUS OBJECTS WITHOUT FERROMAGNETIC COUPLING

(71) Applicants: Sergey A Vinogradov, San Antonio, TX (US); Glenn M Light, San Antonio, TX (US)

(72) Inventors: Sergey A Vinogradov, San Antonio, TX (US); Glenn M Light, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 131 days.

(21) Appl. No.: 14/804,778

(22) Filed: Jul. 21, 2015

(65) Prior Publication Data
US 2017/0023531 A1    Jan. 26, 2017

(51) Int. Cl.
*G01N 29/24* (2006.01)
*G01N 27/82* (2006.01)
*H01F 7/02* (2006.01)
*G01N 29/04* (2006.01)

(52) U.S. Cl.
CPC ......... *G01N 29/2412* (2013.01); *G01N 29/04* (2013.01); *H01F 7/0278* (2013.01); *G01N 2291/0289* (2013.01); *G01N 2291/044* (2013.01); *G01N 2291/0423* (2013.01); *G01N 2291/2696* (2013.01)

(58) Field of Classification Search
None
See application file for complete search history.

(56) References Cited

U.S. PATENT DOCUMENTS

| | | |
|---|---|---|
| 5,456,113 A | 10/1995 | Kwun et al. |
| 5,821,430 A | 10/1998 | Kwun et al. |
| 8,098,065 B2 | 1/2012 | Kwun et al. |
| 8,358,126 B2 | 1/2013 | Light et al. |
| 8,624,589 B2 | 1/2014 | Puchot et al. |

(Continued)

OTHER PUBLICATIONS

Furusawa et al, Mode Control of Guided Wave in Magnetic Hollow Cylinder Using Electromagnetic Acoustic Transducer Array, ScienceDirect, Published Dec. 10, 2014.*

(Continued)

*Primary Examiner* — Melissa Koval
*Assistant Examiner* — Rahul Maini
(74) *Attorney, Agent, or Firm* — Livingston Law Firm

(57) ABSTRACT

A non contact sensor for use in magnetostrictive testing of a solid ferrous structure. In its simplest form, the sensor has a set of permanent magnets arranged in a row with their poles in the same direction, an electrical coil wrapped around the set of magnets, wrapped in direction parallel to the common poles of the magnets, thereby forming a top portion above the set of magnets and a bottom portion below the set of magnets, and a metal shield interposed between the top portion of the coil and the set of magnets. The sensor is operable such that a time varying current in the coil causes guided waves to travel to the structure and to be reflected from anomalies in the structure even when there is no ferromagnetic coupling material between the sensor and the structure.

9 Claims, 4 Drawing Sheets

(56) References Cited

U.S. PATENT DOCUMENTS

| | | | |
|---|---|---|---|
| 2001/0017541 A1* | 8/2001 | Kwun | G01N 22/00 324/240 |
| 2010/0052670 A1* | 3/2010 | Kwun | G01N 29/2412 324/240 |
| 2014/0253110 A1 | 9/2014 | Vinogradov et al. | |
| 2014/0312888 A1 | 10/2014 | Vinogradov et al. | |

OTHER PUBLICATIONS

Yoon Kim et al, "Review of magnetostrictive patch transducers and applications in ultrasonic nondestructive testing of waveguides", Ultrasonics 62 (2015), pp. 3-19, obtained from Science Direct database.*

* cited by examiner

NON-CONTACT MAGNETOSTRICTIVE SENSOR FOR GUIDED WAVE MONITORING OF WIRE ROPES OR OTHER SOLID FERROUS OBJECTS WITHOUT FERROMAGNETIC COUPLING

TECHNICAL FIELD OF THE INVENTION

This invention relates to nondestructive testing using guided wave testing and magnetostrictive sensor technology, and more particularly, to a sensor used for magnetostrictive testing.

BACKGROUND OF THE INVENTION

Magnetostriction is a property of ferromagnetic materials that causes them to change shape when subjected to a magnetic field. Magnetostrictive materials can convert magnetic energy into kinetic energy, or the reverse, and are used to build various actuators and sensors.

For active magnetostrictive testing, elastic waves are launched and reflected echoes of the waves from defects such as corrosion or cracks are detected. Various magnetostrictive actuators have been designed to generate longitudinal waves in rods and cables, torsional waves in pipes, and shear horizontal waves in plates.

Because many systems use the same device for actuating the guided waves as for receiving the reflected waves, magnetostrictive actuator/sensors are often referred to as simply "sensors". Combined actuator/sensor devices are also often referred to as "probes".

Ferromagnetic coupling of a magnetostrictive sensor to the material being tested is an important operative feature of magnetostrictive test systems. Some sensors may make use of magnetostrictive properties of the material being tested, and do not require a magnetostrictive coupling interface, although they do require a contacting sensor.

However, many sensors are made more effective, or are adapted for testing non-ferromagnetic metals, by attaching a ferromagnetic material to the material being tested at areas where the sensors are to be placed. This may be achieved, for example, by coating the surface of the material to be tested with a coat of ferromagnetic material or by bonding a ferromagnetic medium such as wire or ribbon to the surface of the material. Some sensors incorporate a ferromagnetic material into the sensor itself.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

As described in the Background, guided wave testing using magnetostrictive actuators and sensors is a type of non destructive evaluation used for a variety of structures. These actuators and sensors are referred to herein as magnetostrictive "sensors" or "probes".

Various magnetostrictive sensors and techniques are described in the following patents: U.S. Pat. No. 6,396,262 to Light, et al.; U.S. Pat. No. 6,917,196 to Kwun, et al.; U.S. Pat. No. 7,573,261 to Vinogradov; and U.S. Pat. No. 7,821,258 to Vinogradov. Sensors for testing wire ropes are described in U.S. Pat. No. 5,456,113 to Kwun, U.S. Pat. No. 5,821,430 to Kwun et al., and in U.S. Pat. No. 8,098,065 to Kwun, et al. The latter patent describes a sensor having a layer of magnetostrictive material for magnetic coupling to the wire rope. Each of the above-cited patents is incorporated herein by reference.

The sensor described herein is particularly suited for testing of "wire ropes", a term used herein to include various types of cables and other elongated solid structures made from ferrous materials. Typical examples of wire ropes are suspension bridge cables, mooring lines, guy lines, dragline ropes, power transmission lines and ground lines. The sensor can be also used with various metal rods that are not made with individual wires, but rather are a single solid piece of material. In either case, the elongated structure is considered "solid" in the sense that it is not hollow, and is best monitored with compressional guided waves, as opposed to torsional guided waves. The sensor may also be used with hollow structures such as pipelines, although pipelines are not as limited with regard to requiring compressional guided waves.

As stated in the Background, many magnetostrictive sensors use a ferromagnetic strip to provide a contacting interface and to thereby couple the guided waves to the material. A problem with using a ferromagnetic strip for coupling is that a contacting mechanical attachment is not always desirable. For example, in the case of wire ropes, a tight mechanical attachment of the sensor to the wire rope can damage either the sensor or the wire rope.

The following description is directed to a magnetostrictive sensor that does not require a ferromagnetic strip or other physical material for ferromagnetic coupling. The sensor may be non-contact, and is coupled with only electromagnetic coupling propagating through air or other non-ferrous material. Furthermore, because wire ropes can propagate only compressional guided waves, the sensor generates this type of wave in the wire rope.

The sensor described herein is implemented without the need for large magnets, and instead uses a number of small magnets with a polarization vertical (or near-vertical) to the axis of the wire rope. The sensor has a simplified coil design, and thus does not require the use of meander coils, which use Lorenze rather than magnetostriction as the primary force and have complicated configurations.

Figure 1:
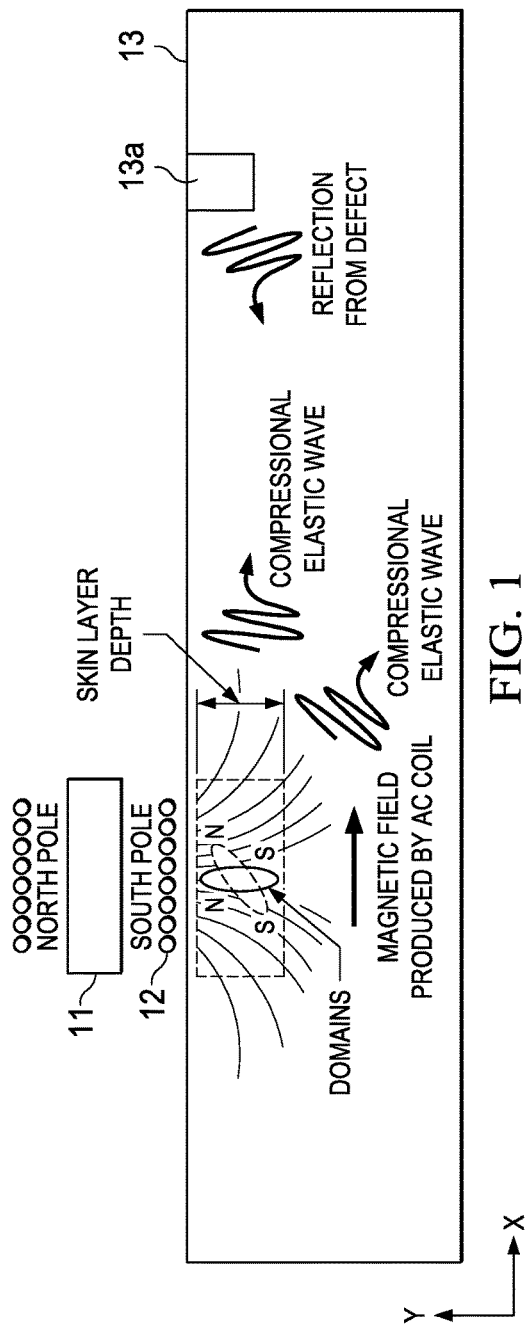
FIG. 1 illustrates the principle of operation of a non contact magnetostrictive sensor.

FIG. 1 illustrates the principle of operation of a non-contact magnetostrictive sensor in accordance with the invention. The sensor is represented by one of its permanent magnets 11 and an AC coil 12.

The sensor is being used to inspect a wire rope 13 having a defect 13a. The wire rope 13 represents various elongated solid ferrous structures, as defined above, that can be tested with the sensor. The wire rope 13 has a skin layer of a predictable depth, through which the magnetic field of magnet 11 can penetrate.

As indicated, the sensor produces compressional elastic waves, which propagate down the length of the wire rope 13. A defect, such as defect 13a, will cause a reflected of guided compressional waves back to the sensor. As explained below, the sensor detects the reflected wave and delivers the detected signal to a monitoring system (described below in connection with FIG. 5). This monitoring system also provides an AC actuation signal to coil 12.

For purposes of this description, the longitudinal length of the wire cable 13 is considered the x-axis. Magnet 11 is a small permanent magnet providing magnetization parallel to the y-axis. This is in contrast to other magnetostrictive sensors, which use large permanent magnets to provide magnetization parallel to the x-axis.

In the example of FIG. 1, the polarization is ninety degrees (vertical) relative to the surface being tested. The same concepts apply for "near-vertical" polarization, defined for purposes of this description as polarization having an angle that may be as much as 45 degrees off vertical. In other words, magnet 11 may be tilted. For simplicity of description herein, the magnets are described as having "vertical" polarization, with the understanding that this may also include "near-vertical".

More specifically, magnet 11 provides a DC bias magnetic field. The initial magnetic domain orientation is parallel to the y-axis (relative to the x-axis of the wire rope). An AC magnetic field provided by coil 12 forces the compressional waves to oscillate in the direction of x-axis. As a result, out-of-plane domain oscillation can be accomplished, producing elastic vibrations in the skin layer of wire rope 13. Because the skin layer is located immediately under the pole of the permanent magnet 11, the delivered permanent magnetic field is sufficiently high for detection even without a ferromagnetic coupling layer.

Once the compressional elastic wave is generated, it travels down the length of the wire rope 13. If the wave encounters change in the cross-section, i.e., defect 13a, a reflected signal is generated. The reflected signal travels back to the probe, and is detected by the probe via the inverse Villary effect. With appropriate system electronics, it is possible to use a single or dual magnetostrictive element for both the transmission and the detection of mechanical waves.

As described below, a sensor implemented with this arrangement of magnets and a coil can be operated at a substantial gap from the surface of the material being tested. For example, a gap of more than several centimeters between the sensor and the wire rope's surface is possible. Thus, as stated above, both the transmission and detection of elastic waves are accomplished without the use of a ferromagnetic coupling interface, such as a ferromagnetic strip. Nor are other couplants, such as water or oil, required.

Figure 2:
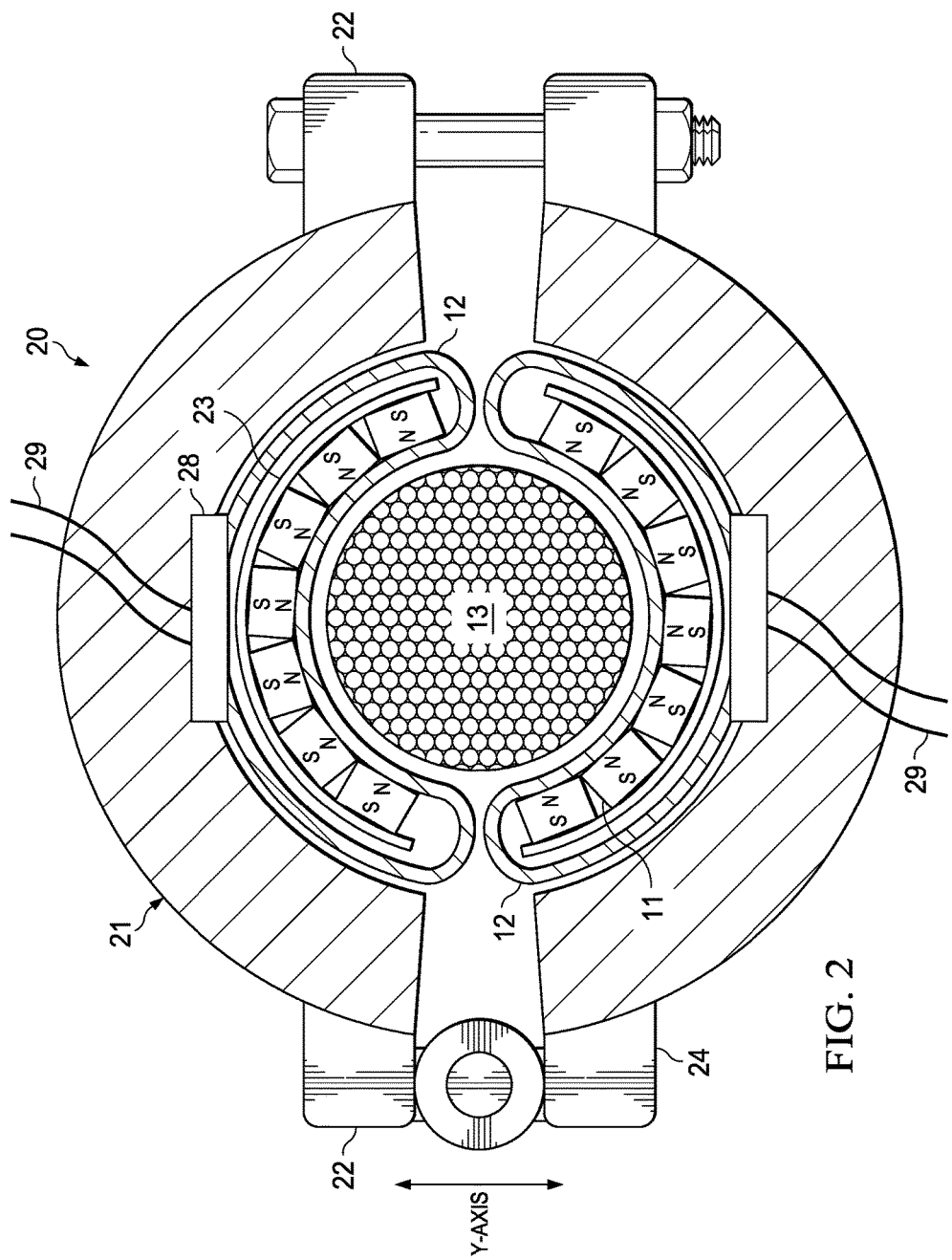
FIG. 2 illustrates a sensor that implements the principles of FIG. 1 and is especially suited for testing wire ropes.

FIG. 2 illustrates a sensor 20 that is configured and operates as described above, in cross sectional view. Sensor 20 is especially designed for use with wire ropes and other elongated longitudinal structures that have a round cross section. However, as explained below, the same concepts can be used for sensors used for other structures, such as non-cylindrical elongated structures or plate structures.

Sensor 20 is ring-shaped and has two halves, for ease of attachment around wire rope 13. These two halves are enclosed in a protective shell 21, which allows sensor 20 to be easily positioned and attached around the circumference of a small section of the wire rope 13. The shell 21 encloses the top and sides of the internal operative elements (magnets 11, shield 23, and coil 12) but does not cover the bottom portion of the sensor 20. As a result, the bottom portion of the coil 12 is spaced from the surface being tested when the sensor is in use.

In the embodiment of FIG. 2, the two halves of sensor 20 form two semi-circles attached with a clamp 22. However, a variety of mechanisms may be use to position and retain the sensor assembly on the wire rope. Other means for securing the sensor 20 might be belts, straps, cable ties, and the like.

The operational elements of sensor 20, i.e., its internal layered structures, are also in two halves and are symmetrical. These internal elements implement the principal of operation of FIG. 1, and comprise a set of small permanent magnets 11 and a coil 12, for each half. The number of sections, i.e., two halves, and the manner and extent to which the wire rope is completely encircled by the sensor, is not significant to the invention, and other configurations are possible.

The coil 12 of each half terminates at an adapter 28 for connection to cables 29. Cables 19 deliver signals between sensor 20 and system instrumentation described below in connection with FIG. 5.

Figure 3:
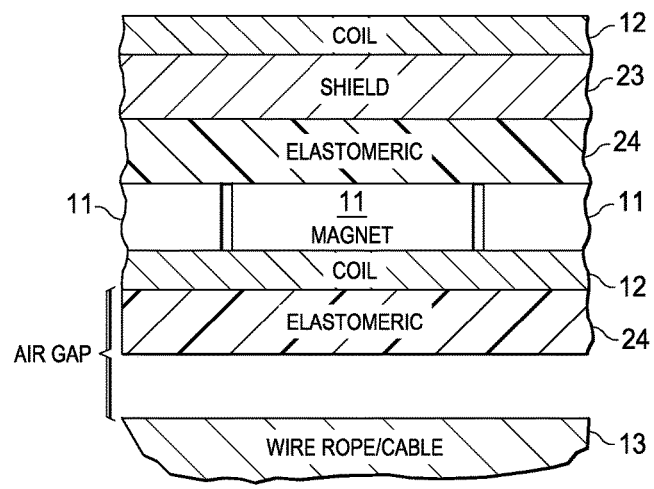
FIG. 3 illustrates the operational layers of a sensor in accordance with the principles of FIG. 1.

FIG. 3 schematically illustrates the sensor's internal layered structures in a partial cross-sectional view. One of the coils 12 is shown as its upper and lower portions, relative to magnets 11, because it is wrapped around magnets 11. These layers may be (but are not necessarily) spaced from wire rope 13 by a gap and comprise thin layers of: coil 12, magnets 11, shield 23, and coil 12.

These layers are typically set in a material, such as an elastomeric material 24, that provides them with a unified flexible structure. The layers may be constructed to allow bending of the sensor around the wire rope, and to accommodate a large range of surface curvatures.

Referring to both FIGS. 2 and 3, the layer of magnets 11 is an array of small permanent magnets. The polarization of each magnet is normal (vertical) to the surface of the wire rope 13, or in other words, along the y-axis. The bottom of the magnets directly interfaces with the surface being tested, but need not be contacting with that surface.

For the example of FIG. 2, in which there are two coils, each coil 12 is wrapped in the direction of the common poles of its set of magnets 11. In other words, because magnets encircle wire rope 13 with the same pole against the surface of wire rope 13, coil 12 is wrapped along (parallel to) and against the common poles. Coil 12 may be formed with multiple parallel conductors at a small spacing.

Figure 4:
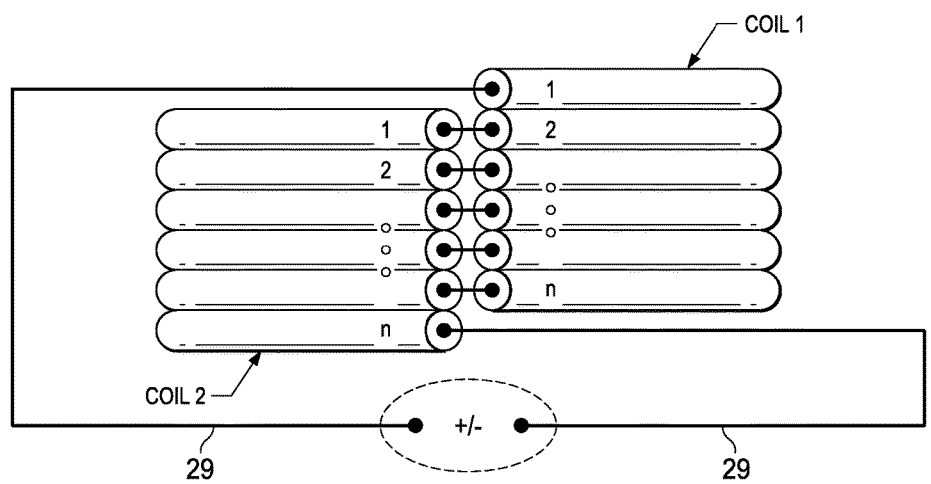
FIG. 4 illustrates how the coils of the sensor of FIG. 3 may be connected to form a single coil for activation and receiving purposes.

FIG. 4 is a schematic of the coil assembly comprising the two coils 12 described above. As described above, both coils 12 are folded and looped over permanent magnets. The exposed conductors at the ends of each coil 12 are shifted from each other by one conductor spacing and joined together so that the parallel conductors in the coil form a flat, flexible, continuous coil with a pair of cable wire leads 29 available for electrical connection to an AC source.

Referring again to FIGS. 2 and 3, shield 23 prevents mutual cancellation of the magnetic fields produced by each AC coil 12. Shield 23 is interposed between the top surface of magnets 11 and the top portion of coil 12.

If desired, a non-contacting relationship between the bottom surface of magnets 11 and the surface of the wire rope can be ensured. For example, padding or spacers could be used to provide a desired amount of spacing and to protect the sensor and the wire rope. For testing wire ropes, if the outer diameter of the wire rope is known, the circular shape formed by the bottom of the sensor can be made to maintain a slightly larger diameter. As explained above, this spacing between the sensor and the surface being tested lessens the likelihood of damage to the sensor or the object being tested.

Figure 5:
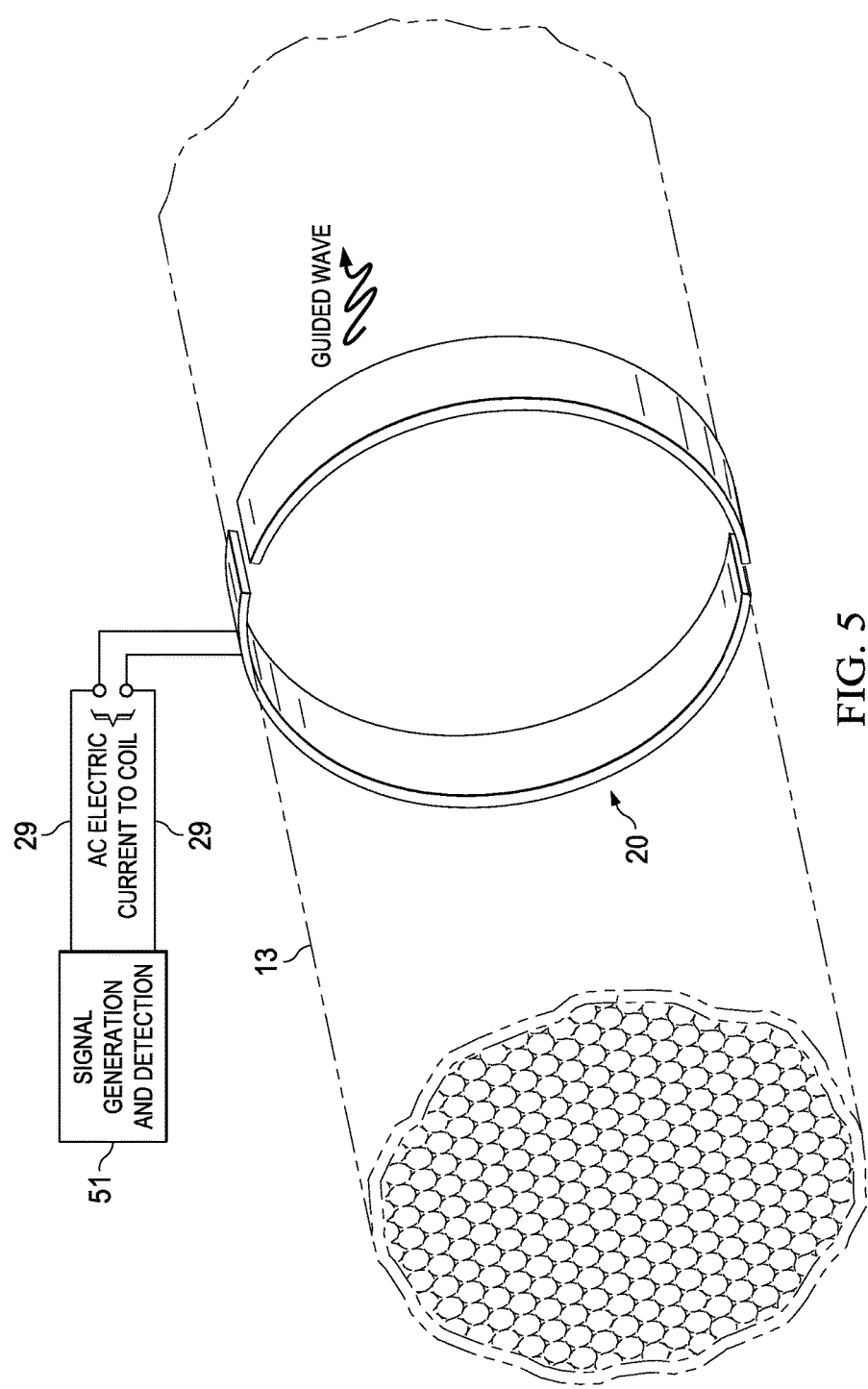
FIG. 5 illustrates a system incorporating the sensor of FIG. 2.

FIG. 5 is a block diagram of electronic instrumentation for implementing a magnetostrictive testing method with the sensor 20, or an equivalent configuration of magnets and coil(s), as illustrated in FIG. 1-4 or 6. Here, sensor 20 is used for both delivering guided waves and receiving reflected signals.

As stated above, magnets 11 provide a DC magnetic field. Coils 12 provide an AC electric field, and have electrical leads 29 for connection to an AC source.

A signal generation and detection unit 51 applies an AC current pulse to the coil assembly comprising coils 12. Signal generation and detection unit 51 also detects the voltage signals induced in the coil assembly by guided waves reflected back from irregularities such as defect 13a.

The same concepts illustrated in FIG. 1 can be implemented with sensors for magnetostrictive testing of structures other than wire ropes. For testing tubular structures that are not exactly circular in cross section, sensor 20 will generally conform to (although it need not contact) the outer diameter of the surface being tested, rather than having the circular geometry of FIG. 2.

Figure 6:
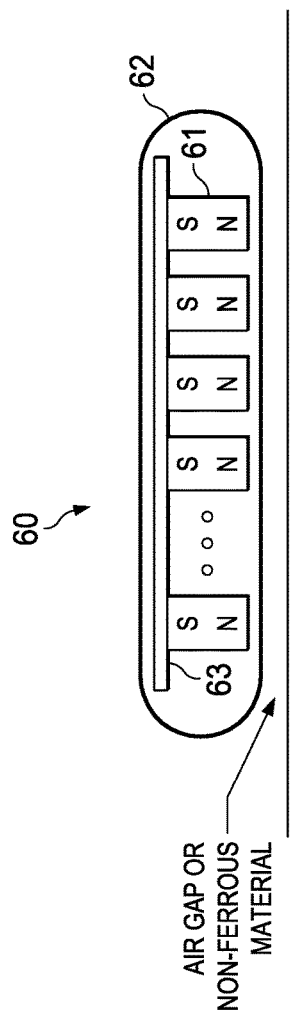
FIG. 6 illustrates a sensor that implements the principles of FIG. 1 and is especially suited for testing plate surfaces.

FIG. 6 illustrates a sensor 60 having a single coil configuration. Sensor 60 is also flat, for testing planar structures, and may be laid flat on the surface of the structure. Alternatively, sensor 60 may be spaced from the surface, with spacers or padding (not shown). Like sensor 20, sensor 60 does not require any physical ferromagnetic coupling material. Sensor 60 typically has a rectangular shape, with the layers of FIG. 3 being flat.

Like sensor 20, sensor 60 comprises a row of small magnets 61 with their polarization in the same direction. A coil 62 is wrapped around the magnets parallel to the common poles. A shield 63 serves the same function as described above. This single coil configuration could be flexible to allow it to be wrapped around curved surfaces, in a manner similar to the sensor of FIG. 2. Because the sensor is non-contact, the sensor's bottom surface (the bottom portion of the coil) need not exactly conform to the surface under test.

What is claimed is:

1. A non-contact sensor for use in magnetostrictive testing of an elongated longitudinal structure, comprising:
    a set of permanent magnets arranged in two semicircles, with all the magnets having the same polarity, such that when the sensor is placed around the circumference of the structure, the magnetic polarization is vertical or near-vertical to the surface of the structure, and the same polarization is directed inwardly into the surface;
    an electrical coil wrapped around the set of magnets, wrapped in a direction parallel to the common poles of the magnets, thereby forming a top portion above the set of magnets and a bottom portion below the set of magnets, such that the bottom portion of the coil is the lowermost element of the sensor; and
    a metal shield interposed between the top portion of the coil and the set of magnets;
    wherein a time varying current in the coil causes compressional guided waves to travel to the structure and to be reflected from anomalies in the structure even when there is no ferromagnetic coupling material between the sensor and the structure and there is a only an air gap between the lowermost element of the sensor and the surface of the structure.

2. The sensor of claim 1, wherein the structure is an elongated longitudinal structure, and the sensor is sufficiently flexible to be wrapped around at least a portion of the outer cross-sectional surface of the structure.

3. The sensor of claim 1, wherein the structure is an elongated longitudinal structure, and the sensor is ring-shaped for placement around a circumference of the structure.

4. The sensor of claim 1, wherein the structure is a planar structure, and the magnets, coil and shield are arranged in planar layers.

5. A sensor for use in magnetostrictive testing of a solid cylindrical structure, comprising:
    a pair of coil assemblies, each coil assembly being semicircular in shape, and each having the following elements: a set of permanent magnets arranged in a row with their poles in a direction vertical or near-vertical to the surface being tested; an electrical coil wrapped around the set of magnets, wrapped in a direction parallel to the common poles of the magnets, thereby forming a top portion above the set of magnets and a bottom portion below the set of magnets; and a metal shield interposed between the top portion of the coil and the set of magnets;
    wherein the bottom portion of the coil is the lowermost element of the sensor;
    wherein the coils are electrically connected to form a single coil for purposes of electrical activation;
    wherein a time varying current in the coil causes guided waves to travel to the structure and to be reflected from anomalies in the structure even when there is no contact between the coil and the structure; and
    a housing for enclosing the coil assemblies except for the bottom portion of the coil, the housing having a circular shape that can be opened and closed around the circumference of the cylindrical structure, and attached to the cylindrical structure such that the there is only an air gap between the lowermost element of the sensor and the surface of the structure.

6. The sensor of claim 5, wherein the coils of each coil assembly are electrically connected to operate as a single coil for receiving activation signals.

7. A method of using a magnetostrictive sensor for testing of a structure, comprising: placing a magnetostrictive sensor against the surface of the structure, the sensor comprising a set of permanent magnets arranged in a row with their poles in the same direction vertical or near-vertical to the surface of the structure; an electrical coil wrapped around the set of magnets, wrapped in a direction parallel to the common poles of the magnets, thereby forming a top portion above the set of magnets and a bottom portion below the set of magnets, such that the bottom portion of the coil is the lowermost element of the sensor; and a metal shield interposed between the top portion of the coil and the set of magnets; applying an AC current to the coil; wherein the sensor is operable to generate waves within the structure and to receive waves reflected from aberrations in the structure when there is only an air gap between the lowermost element of the sensor and the surface of the structure.

8. The method of claim 7, wherein the structure is cylindrical and the sensor is ring shaped.

9. The method of claim 7, wherein the structure is planar and the sensor is planar.

\* \* \* \* \*